United States Patent [19]

Robbins et al.

[11] 4,239,964

[45] Dec. 16, 1980

[54] METHOD FOR URANIUM DETERMINATION

[75] Inventors: John C. Robbins, Alliston; John D. Kinrade, Ottawa, both of Canada

[73] Assignee: Scintrex Limited, Concord, Canada

[21] Appl. No.: 955,787

[22] Filed: Oct. 30, 1978

Related U.S. Application Data

[63] Continuation-in-part of Ser. No. 879,647, Feb. 21, 1978, which is a continuation-in-part of Ser. No. 693,212, Jun. 4, 1976, abandoned.

[51] Int. Cl.$^2$ .................... G01V 5/00; G01N 21/38
[52] U.S. Cl. .................... 250/255; 250/461 R
[58] Field of Search .......... 250/458, 459, 461 R, 250/255, 253, 303, 365, 373; 23/230 EP, 230.3

[56] References Cited

FOREIGN PATENT DOCUMENTS 2438888 2/1976 Fed. Rep. of Germany ...... 250/461 R

OTHER PUBLICATIONS

R. Measures et al., "Analyzing Fluorescence Decay", Laser Focus, 11-74, pp. 49-52.

Primary Examiner—Alfred E. Smith
Assistant Examiner—Carolyn E. Fields
Attorney, Agent, or Firm—Fetherstonhaugh & Co.

[57] ABSTRACT

This invention is a method that uses the previously undiscovered fact that the phosphorescent lifetime of the uranyl ion at very dilute concentrations in an aqueous solution is anomalously long in comparison to that of other commonly-occurring phosphorescent species, wherein the uranyl ions in the low concentration sample are excited by projecting electromagnetic energy into the sample, terminating the projection of electromagnetic energy into the sample and measuring the characteristics of the decaying uranium phosphorescence after termination of the incident electromagnetic radiation.

26 Claims, 6 Drawing Figures

METHOD FOR URANIUM DETERMINATION

This invention relates to a method for detecting uranium compounds in solutions where they are present in very low concentrations, less than about 1 part per million, and is a continuation in part of application Ser. No. 879,647 filed Feb. 21, 1978, to be issued as a patent, which is a continuation in part of application No. 693,212, filed June 4, 1976, now abandoned.

It is not broadly new to identify a compound in a solution or in a crystalline form by subjecting it to electromagnetic radiation to cause it to phosphoresce, terminating the radiation and measuring the intensity of the decaying phosphorescence at a time delay after termination. Compounds which phosphoresce in response to electromagnetic radiation have a lifetime of phosphorescence which in some cases may be characteristic of that compound. Thus, with knowledge of the emission wavelengths of phosphorescence and the relevant lifetimes, one can identify the presence of a certain species in solution or crystalline structure.

In order for the method to work well, however, the substance to be detected must phosphoresce intensely in response to radiation and should also have a lifetime of phosphorescence that is significantly different to any other phosphorescent compounds with which it may be mixed and from which it is desired to be distinguished.

The terms fluorescence, phosphorescence and luminescence, as applied to the radiation emitted by some substances on being irradiated by a source of electromagnetic energy of suitable wavelengths, are now defined. Fluorescence applies to radiation emitted during the time that the substance is illuminated but that decays very rapidly if the irradiation is interrupted. Some substances show a persistence of emission, after the excitation is terminated, that may last for a few microseconds to many seconds or even longer. This is known as phosphorescence. Luminescence is used herein as a general term for radiation emitted where the presence or absence of persistence is not specified.

Contrary to indications of the available literature, we have found that at very low concentrations of uranium, U less than about one part per million, the half life of phosphorescence of uranium compounds in solution increases sharply as the concentration decreases, with the result that the half life of phosphorescence of uranium in such a solution is anomalously long with respect to non-uranium compounds associated therewith. Thus, uranium compounds can be resolved from other phosphorescent species by this anomalous half life of phosphorescence.

Prior to this invention, the half life of phosphorescence had not been used as a diagnostic method to analyse for uranium in a sample. Uranyl compounds have a well known characteristic green luminescence which can be isolated by optical filters and measured as to intensity with a photo detector to give an indication of the uranium concentration in a sample, and presently-used methods for determining the presence of uranium in a sample use this principle. In accordance with one of the more common methods, the liquid sample thought to contain a uranium compound is first evaporated carefully to dryness and the residue is fused at a high temperature with a carbonate-fluoride flux to produce a solid disc. The disc is then placed in an optical fluorimeter where it is illuminated by ultraviolet light to cause uranium present to fluoresce. The characteristic green fluorescence is isolated and measured as an indication of the uranium content of the sample.

The complexity of the foregoing method is apparent. It is also subject to many practical problems arising from the irreproducible chemical and physical characteristics of the disc as commonly prepared.

This invention avoids the necessity of evaporating to dryness and fusing to produce a solid disc. With the method of this invention, one merely projects electromagnetic radiation into a solution thought to contain the uranium, terminates the projection of the radiation and measures the intensity of the decaying uranium phosphorescence at an appropriate time delay after termination of the ultraviolet light.

It is an object of the invention to provide an efficient method that is inexpensive and that can be used in the field as well as in a laboratory, for detecting uranium compounds in solutions where they are present in low concentrations.

With these and other objects in view, this method relates to a method of detecting uranium compounds in a translucent sample through utilization of the anomalously long life time of life time of phosphoresence of the uranyl ion in concentration levels of less than about one part per million, comprising the steps of exciting the uranyl ions in the sample by projecting electromagnetic energy; terminating said projection of electromagnetic energy into the sample; and measuring the decay with time of the uranium phosphorescence after the termination of the incident electromagnetic radiation.

The invention will be clearly understood after reference to the following detailed specification read in conjunction with the drawings.

IN THE DRAWINGS

As indicated above, this invention makes use of the known fact that under excitation by ultraviolet light, uranium compounds phosphoresce with emission of a characteristic green light. It is believed that only hexavalent uranium, $U^{6+}$, present in the uranyl ion, $UO_2^{++}$, phosphoresces, uranium of other valences being essentially non-luminescent.

One of the important aspects of this invention is the discovery that at very low concentrations (U less than one part per million) the half-life of phosphorescence of uranium in an aqueous solution increases very rapidly as the concentration decreases.

The half-life or lifetime of phosphorescence can be defined as follows. Under continuous excitation a fluorescent substance emits a continuous luminescence. If, however, the excitation is abruptly terminated, the luminescence does not decay immediately but over a finite length of time. This decay commonly follows an exponential form:

$$I_t = I_o e^{-Kt} \qquad \text{Equation 1.}$$

where $I_t$ is the intensity at time t;

$I_o$ is the intensity at the moment the excitation is interrupted;

and K is a constant. The lifetime is defined here as the time for which $I_t = I_o e^{-1}$ or $0.37 I_o$.

Figure 1:
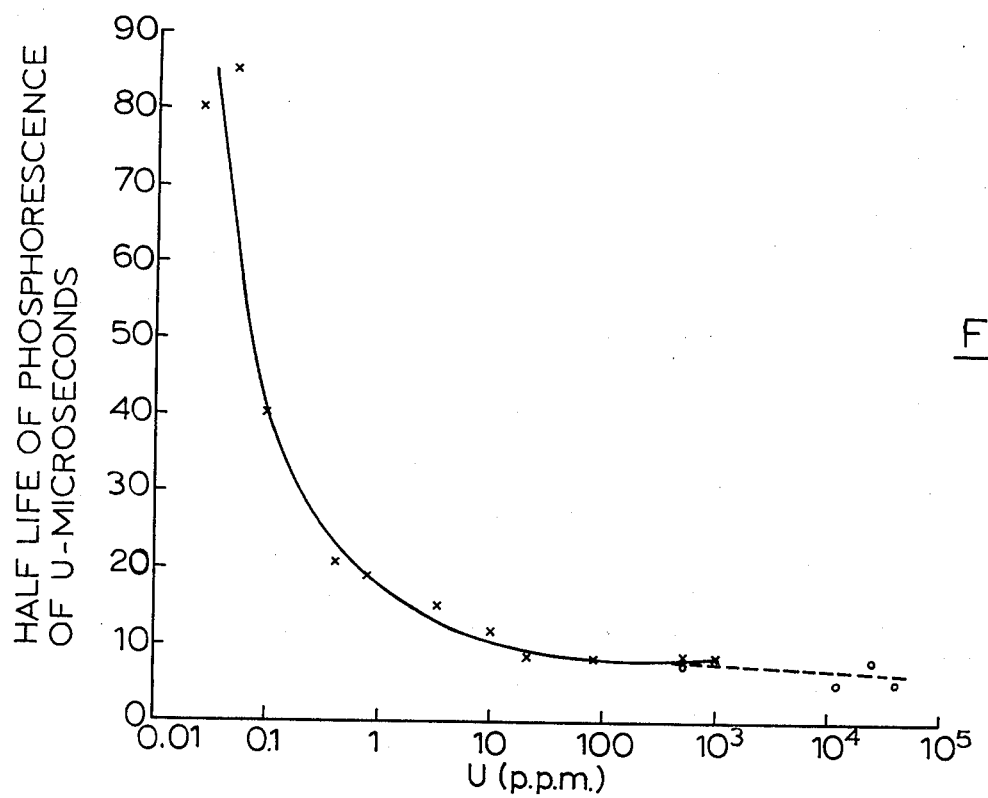
FIG. 1 is a graph illustrating the variation of the time constant of decay of intensity of the phosphorescence of hexavalent uranium, with the concentration of uranium, in an aqueous solution.

The published literature indicates that for simple uranyl forms (i.e., uranyl nitrate, perchlorate) in water solution the lifetime is of the order of 1 to $4 \times 10^{-6}$ sec. Moreover, Benson et al. (Chem. Phys. Letters, V. 35, p. 195, 1975) wrote that although the decay becomes longer at decreasing $UO_2^{++}$ concentrations, their data indicated that at infinitely dilute concentrations an extrapolated value of $6 \times 10^{-6}$ secs would pertain. These measurements were made over a range of about 0.01–2.0 mil/liter (approximately $4 \times 10^3 - 800 \times 10^3$ ppm). We have, however, found that below about ten parts per million U there is instead a very marked progressive increase of lifetime from about $8 \times 10^{-6}$ sec at 70 ppmU, more or less as shown in the literature, to more than $80 \times 10^{-6}$ sec at 50 ppbU. This is shown in FIG. 1 where the points marked o represent data taken from Benson and the points marked x represent data obtained by the present inventors and which are used in the practice of this invention.

This finding is of practical significance because in many real samples, as opposed to laboratory standard solutions which are usually made up in deionised water, there are fluorescent species present other than uranium.

In general, however, the more highly fluorescent the species, the shorter is the corresponding lifetime. For instance, many organic compounds, which might be of either synthetic or natural origin, fluoresce intensely; but their lifetime is measured as a few nanoseconds. For given intensities of luminescence, the greater the difference between the luminescent lifetime of desired species and that of the interference, the lower the level of the former that may be detected. For the data given by Benson et al., a practical system for sub-ppb U levels would not be possible for most natural waters because the uranyl lifetimes are not sufficiently different from the luminescent lifetimes of other compounds likely to be present.

Figure 2:
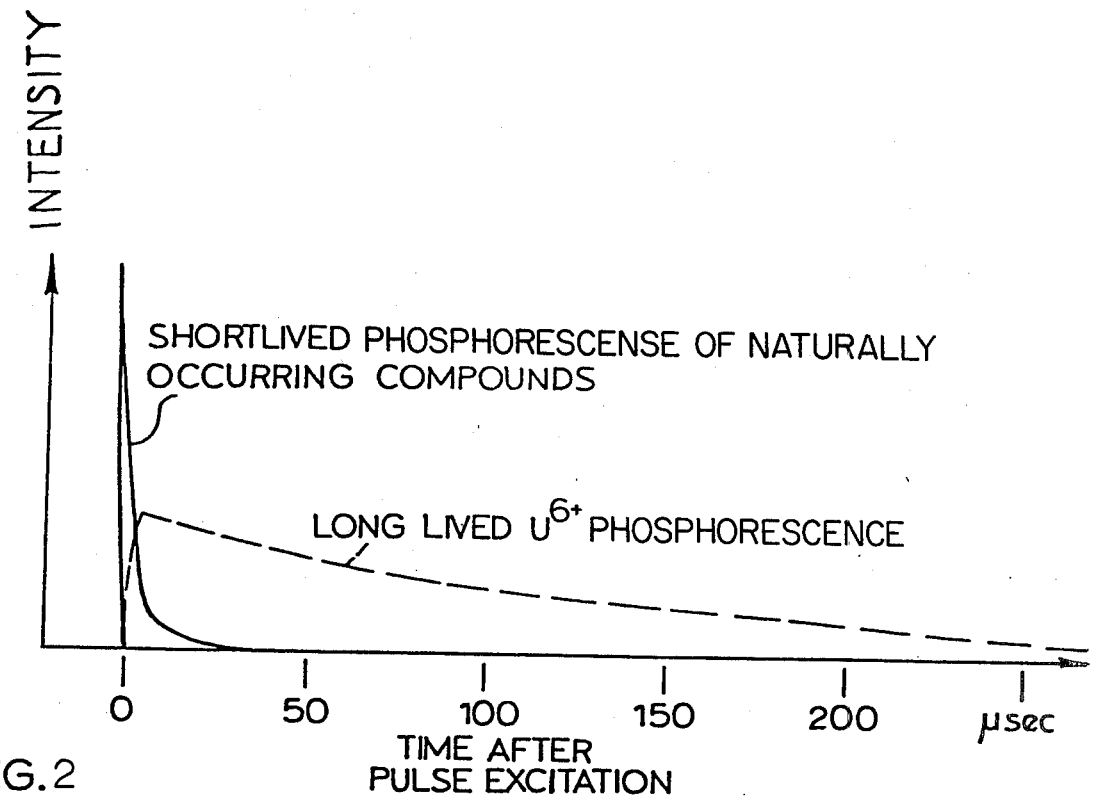
FIG. 2 is a graph illustrating the decay with time of the intensity of phosphorescence of hexavalent uranium in an aqueous solution, at a concentration of less than one part per million and the decay with time of luminescence due to naturally occurring compounds in natural waters.

FIG. 2 is an illustration which compares the decay of the intensity of the phosphorescence of organic compounds found in natural waters after excitation by an ultraviolet light with the corresponding intensity of the phosphorescence of a uranium compound. An examination of the graph shows that after 15 microseconds, all phosphorescence had decayed except that of uranium. By making a measurement at a time after phosphorescence due to the other compounds in the solution was essentially low but before the phosphorescence due to uranium has decayed, one can detect the presence of a uranium compound and, by measuring its intensity, determine the uranium content quantitatively.

A further reason for working at very dilute levels of uranium is as follows: Uranium at relatively high concentrations in real samples (e.g. the aqueous solution obtained from the acid digestion of a geological sample) is almost invariably accompanied by other metal species that quench or reduce to a varying degree the intensity of fluorescence. The degree of quenching due to a given species depends on the concentration of that species but is independent of the uranyl concentration. An important benefit of the practice of the present discovery is that by diluting the sample to the very low levels of uranium exhibiting the "anomalous" lifetime, the quenching effects of interfering species are significantly reduced.

It is considered that the method of this invention is useful at uranium concentrations of less than about one part per million. Typically, natural waters away from uranium bearing mineralization might contain 0.1 ppb uranium or less, but waters draining or in contact with such mineralization might contain 1 to 100 ppb uranium. These concentrations are very much below one ppm. From an examination of the curve of FIG. 1, it will be apparent that the half-life of phosphorescence of any uranium compound that might be present is anomalously long and the detection of uranium compounds would be correspondingly easy. The method, therefore, is important in the exploration for uranium.

In cases where the uranium content is thought or shown to be more than the optimum range for detection by the method, one would dilute the sample progressively to bring it down to a sufficiently low uranium concentration where the half-life of phosphorescence would be anomalously long.

As another aspect of this invention, we have found, at the low uranium concentrations mentioned earlier, that the effect of adding certain anions, notably polyphosphates, to the sample to be tested is to increase markedly the initial quantum yield, that is the quantity, $I_o$, of equation 1. At the same time the lifetime either remains constant or is only slightly reduced. We have also found that there is no enhancement of organic luminescence by the addition of these anions and, thus, such addition can be used to enhance the uranium luminescence selectively.

Figure 4:
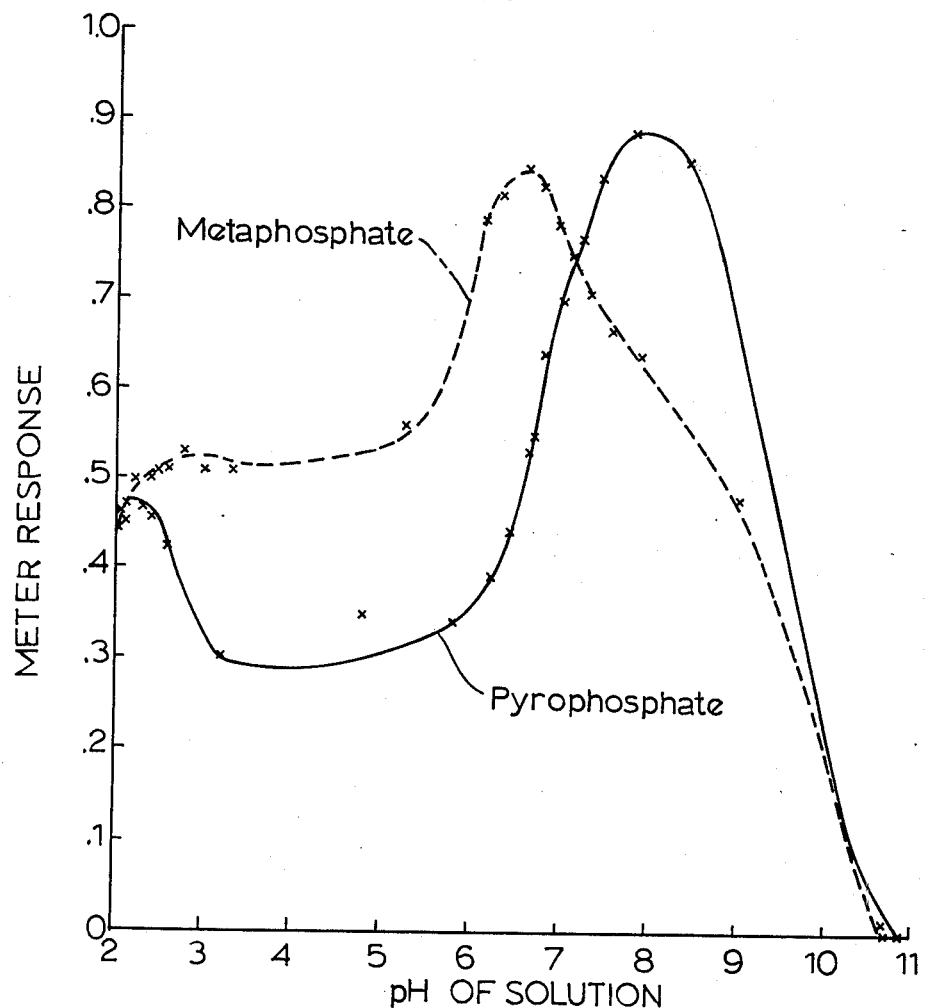
FIG. 4 is a graph which shows the variation of the luminescent intensity of a uranyl solution containing pyrophosphate and metaphosphate with the pH of the solution.

We have found the effect of the phosphorescence enhancement is pH-dependent. The variation of phosphorescence intensity with pH for pyrophosphate and metaphosphate additives is illustrated in FIG. 4. For consistency of instrument calibration the pH of the solution is maintained at the optimum value for phosphorescent intensity.

The normalized relative yield is the ratio of intensity of phosphorescence of a dilute uranyl solution (2 ppbU) to which the polyphosphate reagent has been added compared to the emission of that same solution but without the addition of the reagent. Table 1 illustrates the normalized relative yield for various polyphosphate additives.

TABLE 1

| ADDITIVE | FORMULA | NORMALIZED RELATIVE YIELD |
|---|---|---|
| Sodium pyrophosphate | $Na_4P_2O_7$ | 80 |
| Sodium tripolyphosphate | $Na_5P_3O_{10}$ | 44 |
| Sodium metaphosphate | $(NaPO_3)_{13}$ | 80 |
| Sodium trimetaphosphate | $Na_3P_3O_9$ | 40 |

Although sodium salts of the polyphosphate anions were used in the experiments described in this table, the nature of the anion is not important and any convenient soluble salts of the polyphosphate anion would be effective. Thus, a phosphate taken from the group pyrophosphate, tripolyphosphate, tetraphosphate, trimetaphosphate, tetrametaphosphate and hexametaphosphate is effective.

This family of reagents is sensitive to acid and will decompose eventually to simple monophosphates in highly acidic solutions, more rapidly if the solutions are warmed much above 70° F. The monophosphate solution so generated is considerably less effective in stimulating the luminescent efficiency of the uranyl ion. A buffer is, therefore, added to reduce the acidity of the solution.

While there is a difference in the effect of the polyphosphates listed in Table 1 they are all suitable for the invention.

In all cases listed, the polyphosphate was added to the buffer in the ratio of about 1 to 10. Prior to the uranium analysis the polyphosphate-buffer solution is added to the sample in approximately a 1.0 to 10 ratio. Due to the viscosity of the reagent, care must be taken to ensure that the sample is stirred or otherwise agitated to obtain a homogeneous mixture.

Figure 5:
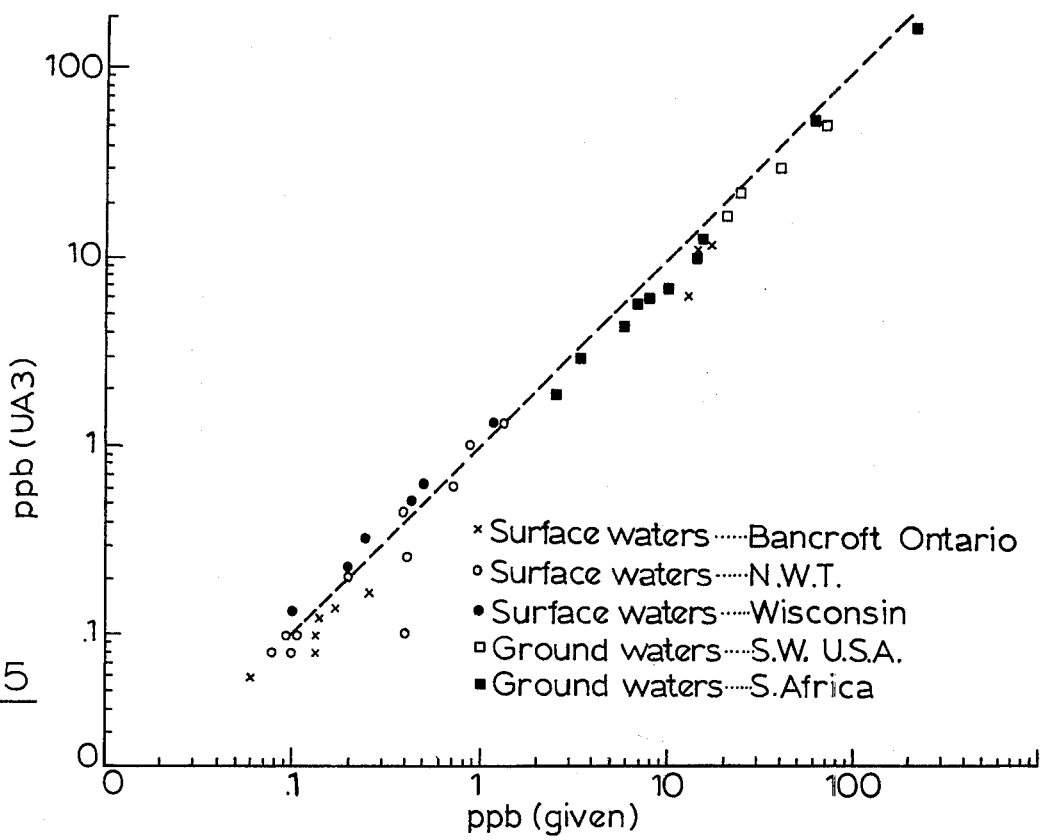
FIG. 5 shows the correspondence between some analyses for uranium using this invention and by other techniques of analysis on samples of natural waters.

Sample waters as indicated were tested by conventional methods and also by this invention. FIG. 5 illustrates the correspondence of results by conventional methods and by the method of this invention. In the Figure the conventional results were represented by a horizontal axis and the results by the method of this invention were represented by a vertical axis. The result is substantially a straight line at 45° indicating similarity of result by both methods.

Figure 3:
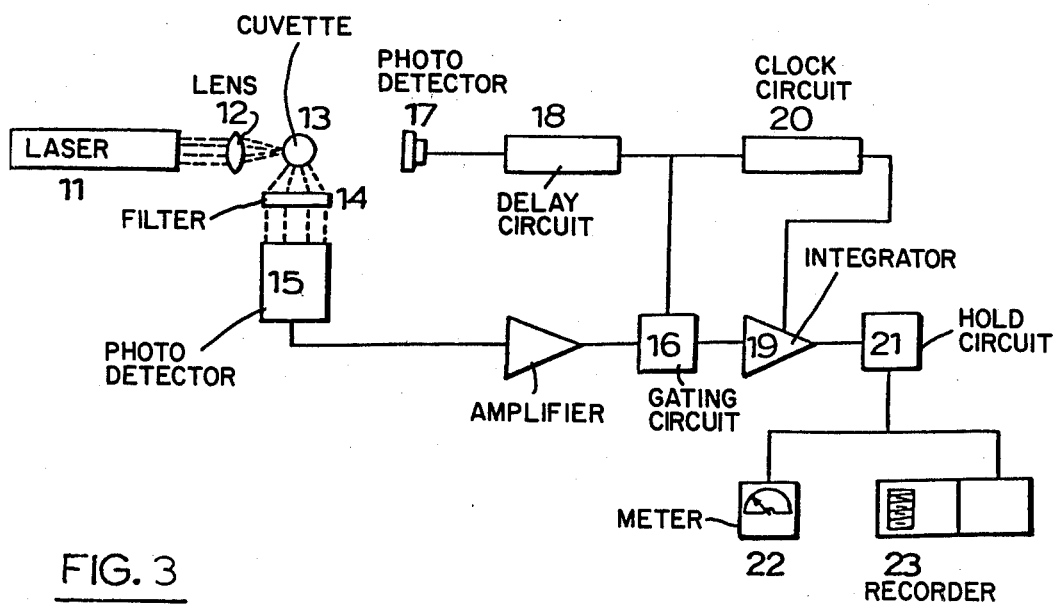
FIG. 3 is a block diagram of apparatus for practising the invention.

FIG. 3 is a block diagram of apparatus for practising the invention. A laser 11 generates a short but intense ultraviolet light pulse. In the embodiment illustrated, the laser is a nitrogen laser which delivers a peak power of about 20 kilowatts at a wave length of 3371° Angstrom or 337.1 nanometers, in a pulse that lasts about 10 nanoseconds. The pulse rate of the laser is 15 per second and it consumes about 5 watts of electrical power.

A lens 12 focuses the laser beam into a transparent cuvette 13 that contains a liquid sample to be tested and a buffered polyphosphate additive, so that any uranium compound in the sample will phosphoresce in response to ultraviolet light. The resultant green phosphorescence of any uranyl compound that might be in the sample is isolated by an optical filter 14 before irradiating the photocathode surface of the photodetector 15. The filter 14 can be a thin-film filter or a suitable liquid filter.

The output of the photodetector 15 is amplified and fed to an electronic gating circuit 16. A second photodetector 17 monitors the incident laser beam. A delay circuit 18 allows only that signal due to phosphorescence attributable to uranium to pass through the gate circuit, by operating to permit passage after termination of a pulse of light from the laser only after a time delay within which signals due to luminescence of most materials other than uranium have dropped to a value at which they are insignificant. The delay period was set at between 10–15 microseconds.

The resulting periodic signal is fed to an integrator 19 which is allowed to accumulate 64 consecutive pulses, after which a "sample and hold" circuit 21 samples the integrator and transfers the information to a meter 22 and recorder 23. Following readout the integrator is reset by an electronic clock circuit 20. The output of the "sample and hold" circuit is proportional to the intensity of the phosphorescence which in turn is proportional to the uranyl ion concentration of the solution. One can, by using known solutions, calibrate the instrument to read uranyl ion concentrations directly. Following readout, it is reset by an electronic clock circuit 20 driven by the trigger circuit, after which, a "sample and hold" circuit 21 samples the integrator and transfers the information to a meter 22 and recorder 23. The time delay after the termination of the projection of the ultraviolet pulse into the sample, after which intensity measurement takes place, is capable of variation and quite feasibly might be as small as 5 microseconds, although time delays of more than 10 microseconds are far preferable. It should be sufficiently long after the termination of the pulse of light so that there will be no electrical noise interference, such as is commonly present from a pulsed laser. The delay also must be longer than the lifetime of luminescence of most other (non-uranyl) compounds in the material that luminesce.

The luminescence of most species commonly found in natural samples intrinsically lasts for nanoseconds, but instrumental effects may "stretch" this lifetime to some 5–10 microseconds. For example, at the sensitivity required for uranyl analysis in the parts per billion range, the photodetector must be run with a high gain and is thus liable to saturation by the intense radiation from the fluorescent species in natural samples. The long lifetime of very dilute uranyl ions enables measurements to be made after such disturbances have decayed.

Sources of ultraviolet light other than a laser beam can be used, although the highly directional properties of such a beam are very desirable. For example, a pulsed Zenon arc lamp might be used, which has, however, an output ranging from the ultraviolet to the infrared and would thus require considerable spectral filtering to avoid light scattering. The nitrogen laser is to be preferred because it has significant output at only one wave length (337 nm) although it is not thought of as the only possible source of ultraviolet light that can irradiate the sample.

Ultraviolet light is not considered as the only possible excitation source. In fact, other electromagnetic energy sources providing wave lengths of less than about 450 nanometers, which is the maximum wave length that can be used to excite uranyl phosphorescence, can also be employed.

The laser repetition rate in the example given of 15 pulses per second was conveniently locked to a sub-harmonic of the frequency of the power supply, the frequency of this being 60 cycles per second. Increasing the pulse frequency would improve the detection limit for a given period of signal integration, but at the expense of increased laser power consumption.

In a typical uranium measurement, the nitrogen laser is set to deliver about 20–30 kilowatts peak power in a beam focussed onto a small cuvette into which some 5–10 ml of the liquid sample, including reagent, is placed. A filter with a spectral response optimized for uranium phosphorescence (480–540 nm) was used in front of the photomultiplier. A small silicon photodiode monitored the intensity of fluorescence due to organic species in the sample. With such a detector system and suitable electronics, recorder responses of the order of 10 V per ppb uranium are obtained. Detection limits of 0.03 ppb uranium have been achieved.

The effect of interfering ions has been checked to verify the efficacy of the buffer-polyphosphate additive. It has been found that useful uranium analyses can be made even in the presence of as much as 10–100 ppm quantities of $Cl^-$ and $CO_3^{--}$ and 10–50 ppm levels of Fe and $Mn^{++}$—levels that would otherwise have effectively made such measurements impossible.

The readout of the instrument is calibrated to yield concentrations of uranyl ion of very much less than one part per million because, as noted above, it is in this range where the half-life of uranyl phosphorescence is optimized and maximum rejection of fluorescent interferences can be expected. If a sample tested is believed to have a higher concentration of uranium the sample is progressively diluted by known ratios until a concentration within the normal range of the instrument is obtained. From the scale reading and the amount of dilution necessary to obtain it one can determine the concentration of the uranyl ion of the original solution.

Persons skilled in the art may determine other techniques for using the basic method which makes use of the present discovery of the anomalously long half-life of decay of uranyl phosphorescence in low concentration solutions.

FIG. 5 shows a comparison of uranium analyses made on samples of natural waters using the present invention (designated UA-3 in this embodiment), with those made on the same samples by either fused-disk fluorimetry or fission-track analyses. The range of uranium concentrations was from 0.05 to 200 ppb. The correspondence between these two sets of data is excellent and proves the potential accuracy of measurements made using this invention.

Figure 6:
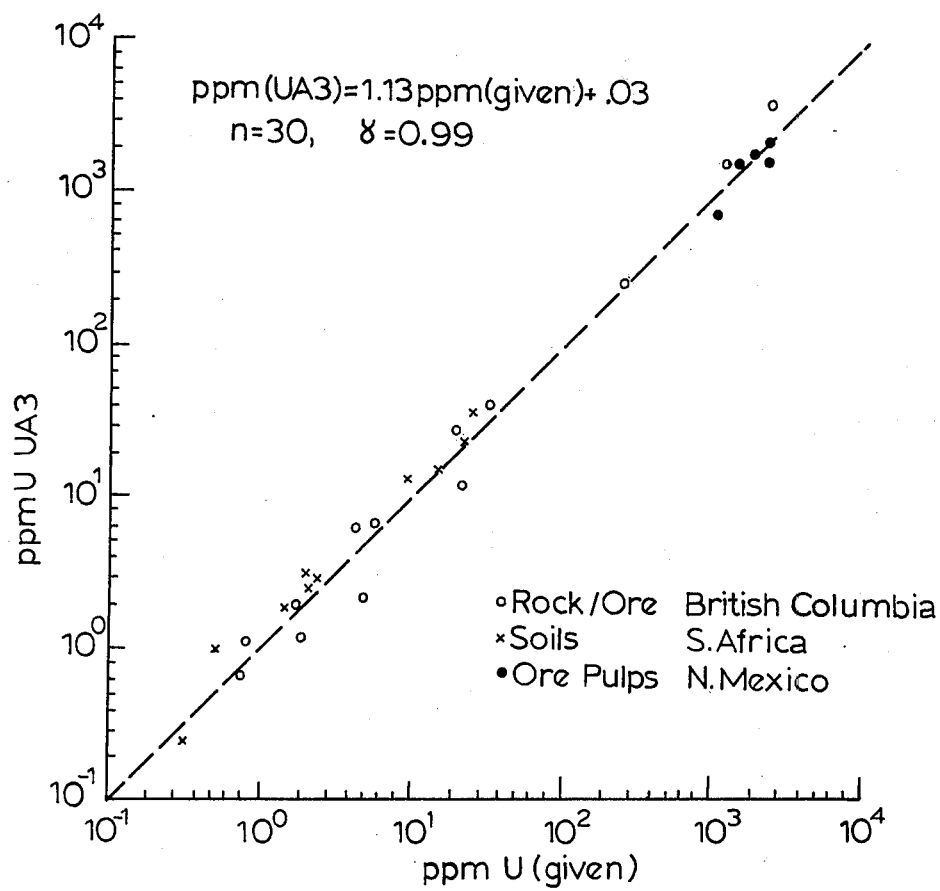
FIG. 6 shows a similar correspondence diagram for solid samples of geological origin.

FIG. 6 shows a similar comparison diagram of analyses made on solutions derived from solid samples (soils, silts and rocks). The range of uranium concentrations herein was from about 300 ppb to 2000 ppm. For these measurements the uranium was first extracted from the sample by acid digestion and then appropriately diluted with deionised water to less than 1 ppm before analysis with the UA-3. The straight line graph is a testament to the accuracy of the method of this type of analysis.

Whereas the foregoing discussion has largely referred to uranium compounds in an aqueous solution, it is apparent that similar comments will apply to solutions of uranium compounds involving other solvents.

What I claim is:

1. A method of detecting uranium compounds in a translucent sample through utilization of the anomalously long life time of phosphorescence of the uranyl ion in concentration levels of less than about one part per million, comprising the steps of:
   exciting the uranyl ions in the sample by projecting electromagnetic energy;
   terminating said projection of electromagnetic energy into the sample; and
   measuring the decay with time of the uranium phosphorescence after the termination of the incident electromagnetic radiation.

2. A method as in claim 1 including the step of diluting the original concentration of uranium to below the level of about one part per million.

3. A method as in claims 1 or 2 wherein said source of electromagnetic energy is ultraviolet light.

4. A method as in claim 1 or claim 2 wherein said translucent sample is an aqueous solution.

5. A method as claimed in claim 1 or claim 2 including the steps of increasing selectively the phosphorescent characteristics of the uranium compounds by adding a polyphosphate compound.

6. A method as claimed in claim 1 or claim 2 including the steps of increasing selectively the phosphorescent characteristics of the uranium compounds by adding a polyphosphate compound wherein said sample is buffered to maintain a pH between 5 and 10.

7. A method as claimed in claim 1 or claim 2 including the steps of increasing selectively the phosphorescent characteristics of the uranium compounds by adding a polyphosphate compound wherein said sample is buffered to maintain a pH between 6 and 8.

8. A method as claimed in claim 1 or claim 2 including the steps of increasing selectively the phosphorescent characteristics of the uranium compounds by adding a polyphosphate compound wherein said sample is buffered to maintain a pH of about 7.

9. A method as claimed in claim 1 or claim 2 including the steps of increasing selectively the phosphorescent characteristics of the uranium compounds by adding a polyphosphate compound wherein said polyphosphate compound is a polyphosphate compound taken from the group of pyrophosphate, tripolyphosphate, tetraphosphate, trimetaphosphate, tetrametaphosphate and hexametaphosphate.

10. A method as in claim 1 or claim 2 wherein said source of electromagnetic energy is a laser.

11. A method as in claim 1 or claim 2 wherein said translucent sample is an aqueous solution and wherein said source of electromagnetic energy is ultra-violet light.

12. A method as claimed in claim 1 or claim 2 including the steps of increasing selectively the phosphorescent characteristics of the uranium compounds by adding a polyphosphate compound and wherein said source of electromagnetic energy is ultra-violet light.

13. A method as claimed in claim 1 or claim 2 including the steps of increasing selectively the phosphorescent characteristics of the uranium compounds by adding a polyphosphate compound wherein said sample is buffered to maintain a pH between 5 and 10 and wherein said source of electromagnetic energy is ultra-violet light.

14. A method as claimed in claim 1 or claim 2 including the steps of increasing selectively the phosphorescent characteristics of the uranium compounds by adding a polyphosphate compound wherein said sample is buffered to maintain a pH between 6 and 8 and wherein said source of electromagnetic energy is ultra-violet light.

15. A method as claimed in claim 1 or claim 2 including the steps of increasing selectively the phosphorescent characteristics of the uranium compounds by adding a polyphosphate compound wherein said sample is buffered to maintain a pH of about 7 and wherein said source of electromagnetic energy is ultra-violet light.

16. A method as claimed in claim 1 or claim 2 including the steps of increasing selectively the phosphorescent characteristics of the uranium compounds by adding a polyphosphate compound wherein said polyphosphate compound is a polyphosphate compound taken from the group of pyrophosphate, tripolyphosphate, tetraphosphate, trimetaphosphate, tetrametaphosphate and hexametaphosphate and wherein said source of electromagnetic energy is ultra-violet light.

17. A method as claimed in claim 1 or claim 2 including the steps of increasing selectively the phosphorescent characteristics of the uranium compounds by adding a polyphosphate compound wherein said translucent sample is an aqueous solution.

18. A method as claimed in claim 1 or claim 2 including the steps of increasing selectively the phosphorescent characteristics of the uranium compounds by adding a polyphosphate compound wherein said sample is buffered to maintain a pH between 5 and 10 wherein said translucent sample is an aqueous solution.

19. A method as claimed in claim 1 or claim 2 including the steps of increasing selectively the phosphorescent characteristics of the uranium compounds by adding a polyphosphate compound wherein said sample is buffered to maintain a pH between 6 and 8 wherein said translucent sample is an aqueous solution.

20. A method as claimed in claim 1 or claim 2 including the steps of increasing selectively the phosphorescent characteristics of the uranium compounds by adding a polyphosphate compound wherein said sample is buffered to maintain a pH of about 7 wherein said translucent sample is an aqueous solution.

21. A method as claimed in claim 1 or claim 2 including the steps of increasing selectively the phosphorescent characteristics of the uranium compounds by adding a polyphosphate compound wherein said polyphosphate compound is a polyphosphate compound taken from the group of pyrophosphate, tripolyphosphate, tetraphosphate, trimetaphosphate, tetrametaphosphate and hexametaphosphate wherein said translucent sample is an aqueous solution.

22. A method as claimed in claim 1 or claim 2 including the steps of increasing selectively the phosphorescent characteristics of the uranium compounds by adding a polyphosphate compound and wherein said source of electromagnetic energy is ultra-violet light and wherein said translucent sample is an aqueous solution.

23. A method as claimed in claim 1 or claim 2 including the steps of increasing selectively the phosphorescent characteristics of the uranium compounds by adding a polyphosphate compound wherein said sample is buffered to maintain a pH between 5 and 10 and wherein said source of electromagnetic energy is ultra-violet light and wherein said translucent sample is an aqueous solution.

24. A method as claimed in claim 1 or claim 2 including the steps of increasing selectively the phosphorescent characteristics of the uranium compounds by adding a polyphosphate compound wherein said sample is buffered to maintain a pH between 6 and 8 and wherein said source of electromagnetic energy is ultra-violet light and wherein said translucent sample is an aqueous solution.

25. A method as claimed in claim 1 or claim 2 including the steps of increasing selectively the phosphorescent characteristics of the uranium compounds by adding a polyphosphate compound wherein said sample is buffered to maintain a pH of about 7 and wherein said source of electromagnetic energy is ultra-violet light and wherein said translucent sample is an aqueous solution.

26. A method as claimed in claim 1 or claim 2 including the steps of increasing selectively the phosphorescent characteristics of the uranium compounds by adding a polyphosphate compound wherein said polyphosphate compound is a polyphosphate compound taken from the group of pyrophosphate, tripolyphospphate, tetraphosphate, trimetaphosphate, tetrametaphosphate and hexametaphosphate and wherein said source of electromagnetic energy is ultra-violet light and wherein said translucent sample is an aqueous solution.

* * * * *